United States Patent [19]

Vaahs

[11] Patent Number: 4,882,448

[45] Date of Patent: Nov. 21, 1989

[54] SI,SI'DIORGANYL-N-ALKYL-TETRA-CHLORO-DISILAZANES AND A PROCESS FOR THEIR PREPARATION

[75] Inventor: Tilo Vaahs, Kelkheim, Fed. Rep. of Germany

[73] Assignee: Hoechst Aktiengesellschaft, Frankfurt am Main, Fed. Rep. of Germany

[21] Appl. No.: 279,414

[22] Filed: Dec. 2, 1988

[30] Foreign Application Priority Data

Dec. 4, 1987 [DE] Fed. Rep. of Germany ....... 3741060

[51] Int. Cl.$^4$ ................................................ C07F 7/10
[52] U.S. Cl. .................................................... 556/412
[58] Field of Search .......................................... 556/412

[56] References Cited

U.S. PATENT DOCUMENTS 3,393,218 7/1968 Van Wager et al. ............... 556/412
3,755,397 8/1973 Roth et al. ...................... 556/412 X
3,927,057 12/1975 Tahaniezawa et al. ......... 556/412 X

OTHER PUBLICATIONS

J. P. Mooser et al., Z. Naturforsch., 296, 166–173, (1973).

Primary Examiner—Paul F. Shaver

[57] ABSTRACT

The invention relates to a process for the preparation of Si,Si'-diorganyl-N-alkyl-tetrachloro-disilazanes of the formula $RSiCl_2-NR'-SiCl_2R$, in which R is $C_1-C_4$-alkyl, vinyl or phenyl and R' is $C_1-C_4$-alkyl, and to these compounds themselves, with the exception of those where $R=R'=CH_3$. To prepare the compounds mentioned, organyltrichlorosilanes $RSiCl_3$ and monoalkylamines $R'NH_2$ are reacted with one another in an aprotic solvent at $-10°$ C. to $+70°$ C., the molar ratio of $RSiCl_3:R'NH_2$ being at least 0.3:1.

9 Claims, No Drawings

SI,SI'DIORGANYL-N-ALKYL-TETRACHLORO-DISILAZANES AND A PROCESS FOR THEIR PREPARATION

DESCRIPTION

The present invention relates to a process for the preparation of Si,Si'-diorganyl-N-alkyl-tetrachloro-disilazanes of the formula $RSiCl_2-NR'-SiCl_2R$, in which R is $C_1$-$C_4$-alkyl, vinyl or phenyl and R' is $C_1$-$C_4$-alkyl, and to these compounds themselves, with the exception of that where $R=R'=CH_3$. The compound mentioned last is already known and has hitherto been obtained by transsilylation of the completely methylated disilazane $(CH_3)_3Si-N(CH_3)-Si(CH_3)_3$ (J. P. Mooser et al., Z. Naturforsch. 29 b (1974) 166-173):

$(CH_3)_3Si-N(CH_3)-Si(CH_3)_3 + 2(CH_3)SiCl_3 \rightarrow Cl_2(CH_3)Si-N(CH_3)-Si(CH_3)Cl_2 + 2(CH_3)_3SiCl$ This process has the disadvantage that drastic reaction conditions (reflux, reaction time of 40 days) are necessary and aluminum chloride must additionally be added so that a complete reaction is achieved. Trimethylchlorosilane additionally arises as a by-product.

The present invention achieves the object of preparing this compound and a series of its higher homologs in a simple manner.

The present invention relates to a process for the preparation of Si,Si'-diorganyl-N-alkyl-tetrachloro-disilazanes of the formula $RSiCl_2-NR'-SiCl_2R$, in which R is $C_1$-$C_4$-alkyl, vinyl or phenyl and R' is $C_1$-$C_4$-alkyl, which comprises reacting organyltrichlorosilanes $RSiCl_3$ and monoalkylamines $R'NH_2$, in which R and R' have the meaning given, with one another in an aprotic solvent at a temperature of $-10°$ C. to $+70°$ C., the molar ratio of $RSiCl_3:R'NH_2$ being at least 0.3:1.

Preferably, R is methyl, ethyl, vinyl or phenyl and R' is methyl. In particular, R is ethyl and R' is methyl. The molar ratio of $RSiCl_3:R'NH_2$ is preferably 0.3:1 to 1:1, in particular 0.5:1 to 0.7:1. A molar ratio of $RSiCl_3:R'NH_2$ of more than 1:1, for example 2:1, of course is also successful, but such as excess of $RSiCl_3$ is superfluous and the unreacted portion must be separated off from the dichlorosilazane desired.

The reaction temperature is preferably 0° C. to +20° C. Polar aprotic solvents, in particular ethers, are preferably used.

The reaction equation is:

$2RSiCl_3 + 3H_2NR' \rightarrow RSiCl_2-NR'-SiCl_2R + 2H_2NR'\cdot HCl$

Mixtures of the organyltrichlorosilanes give a mixture of the possible disilazanes, for example reaction of the binary mixture of $CH_3SiCl_2$ and $(C_2H_3)SiCl_3$ with $CH_3NH_2$ gives the ternary mixture of $CH_3SiCl_2-N(CH_3)-SiCl_2CH_3$, $(C_2H_3)SiCl_2-N(CH_3)-SiCl_2(C_2H_3)$ and $(C_2H_3)SiCl_2-N(CH_3)-SiCl_2CH_3$.

The Si,Si'-diorganyl-N-alkyl-tetrachloro-disilazanes according to the invention can be converted into polymeric silazanes by reaction with at least 6.7 moles of ammonia per mole of chlorodisilazane in aprotic solvents, preferably tetrahydrofuran, at $-80°$ C. to $+70°$ C., preferably at $-10°$ C. to 0° C. These silazanes can then be converted into ceramic materials containing silicon nitride by pyrolysis in a nitrogen or argon atmosphere at 800° to 1400° C. The polymeric silazanes dissolve in all the customary aprotic solvents. They can be shaped into three-dimensional shaped articles before the pyrolysis, for example by monoaxial or isostatic pressing, slip casting or extrusion.

EXAMPLE 1

50 ml (63.5 g; 0.42 mole) of methyltrichlorosilane were dissolved in 300 ml of dry tetrahydrofuran in a 500 ml three-necked flask with a cold finger and stirring device. The cold finger was cooled to $-78°$ C. (dry ice) and the solution was cooled to $-10°$ C. 25.7 ml (19.8 g; 0.64 mole) of methylamine were now passed in so that the internal temperature did not rise above $-5°$ C. The methyl ammonium chloride formed was filtered off, after warming to 20° C. The filtrate was subjected to fine distillation. 22.5 g of the Si,Si'-dimethyl-N-methyl-tetrachlorosilazane distilled over at 96° C. under 81 mbar (yield 42%).

$^1$H-NMR data: $N(CH_3)$ $\delta=2.8$ ppm, intensity: 1 singlet. $Si(CH_3)$ $\delta=0.95$ ppm, intensity: 2 singlet.

EXAMPLE 2

0.6 mole (96.9 g; 76.3 ml) of vinyltrichlorosilane was dissolved in 700 ml of dry tetrahydrofuran in a 1 l three-necked flask with a cold finger and stirring device. The cold finger was cooled to $-78°$ C. (dry ice) and the solution was cooled to 0° C. 27.9 g (0.9 mole) of methylamine were now passed in.

The methylamine hydrochloride formed was filtered off with suction and the filtrate was subjected to distillation. 50.6 g (0.18 mole; yield 60%) distilled over at 142° C. under 81 mbar.

$^1$H-NMR data in $CDCl_3$: $N(CH_3)$ $\delta=2.85$ ppm singlet. $Si(C_2H_3)$ $\delta=6.2$ ppm multiplet.

EXAMPLE 3

0.6 mole (98.1 g; 79.1 ml) of ethyltrichlorosilane was dissolved in 700 ml of tetrahydrofuran in a 1 l three-necked flask with a cold finger and stirring device. The cold finger was cooled to $-78°$ C. and the solution was cooled to 0° C. 27.9 g (0.9 mole) of methylamine were now passed in.

The methylamine hydrochloric formed was filtered off with suction and the filtrate was subjected to distillation. 107.8 g (0.28 mole; yield 93%) distilled over a 64° C. under 14 mbar.

$^1$H-NMR data in $CDCl_3$: $N(CH_3)$ $\delta=2.87$ ppm singlet. $Si(CH_2H_5)$ $\delta=1.15$ ppm multiplet.

EXAMPLE 4

0.3 mole (48.4 g; 38.1 ml) of vinyltrichlorosilane and 0.3 mole (49 g; 39.6 ml) of ethyltrichlorosilane were dissolved in 700 ml of tetrahydrofuran in a 1 l three-necked flask with a cold finger and stirring device. The cold finger was cooled to $-78°$ C. and the solution was cooled to 0° C. 27.9 g (0.9 mole) of methylamine were now passed in. The methylamine hydrochloride formed was filtered off with suction and the filtrate was subjected to distillation.

43.2 g of a mixture of all three possible isomers distilled over at 70° to 80° C. under 14 mbar.

$^1$H-NMR data of $Cl_2(C_2H_3)Si-N(CH_3)-Si(C_2H_5)Cl_2$ in $CDCl_3$: $N(CH_3)$ $\delta=2.37$ ppm singlet. $Si(C_2H_3)$ $\delta=6.2$ ppm multiplet. $Si(C_2H_5)$ $\delta=1.15$ ppm multiplet.

I claim:

1. A process for the preparation of an Si,Si'-diorganyl-N-alkyl-tetrachloro-disilazane of the formula $RSiCl_2-NR'-SiCl_2R$, in which R is $C_1-C_4$-alkyl, vinyl or phenyl and R' is $C_1-C_4$-alkyl, which comprises reacting an organyltrichlorosilane $RSiCl_3$ and a monoalkylamine $R'NH_2$, in which R and R' have the meaning given, with one another in an aprotic solvent at a temperature of $-10°$ C. to $+70°$ C., the molar ratio of $RSiCl_3:R'NH_2$ being at least 0.3:1.

2. The process as claimed in claim 1, wherein the molar ratio of $RSiCl_3:R'NH_2$ is 0.3:1 to 1:1.

3. The process as claimed in claim 1, wherein the molar ratio of $RSiCl_3:R'NH_2$ is 0.5:1 to 0.7:1.

4. The process as claimed in claim 1, wherein R is methyl, ethyl, vinyl or phenyl and R' is methyl.

5. The process as claimed in claim 1, wherein R is ethyl and R' is methyl.

6. The process as claimed in claim 1, wherein an ether is used as the aprotic solvent.

7. An Si,Si'-diorganyl-N-alkyl-tetrachlorodisilazane of the formula $RSiCl_2-NR'-SiCl_2R$, in which R is $C_1-C_4$-alkyl, vinyl or phenyl and R' is $C_1-C_4$-alkyl, excluding $R=R'=CH_3$.

8. An Si,Si'-diorganyl-N-alkyl-tetrachloro-disilazane as claimed in claim 7, wherein R is ethyl, vinyl or phenyl and R' is methyl.

9. An Si,Si'-diorganyl-N-alkyl-tetrachloro-disilazane as claimed in claim 7, wherein R is ethyl and R' is methyl.

* * * * *